United States Patent
Regenass et al.

[11] Patent Number: 5,827,846
[45] Date of Patent: Oct. 27, 1998

[54] CARBAZOLE DERIVATIVES AS AGENTS AGAINST MULTI-DRUG RESISTANCE

[75] Inventors: Urs Regenass, Ettingen; Giorgio Caravatti, Allschwil; Oskar Wacker, Basel, all of Switzerland

[73] Assignee: Novartis Corp., Summit, N.J.

[21] Appl. No.: 750,155

[22] PCT Filed: May 19, 1995

[86] PCT No.: PCT/EP95/01909

§ 371 Date: Nov. 27, 1996

§ 102(e) Date: Nov. 27, 1996

[87] PCT Pub. No.: WO95/32974

PCT Pub. Date: Dec. 7, 1995

[30] Foreign Application Priority Data

Jun. 1, 1994 [CH] Switzerland .............. 1716/94

[51] Int. Cl.[6] .................................... A61K 31/55
[52] U.S. Cl. ........................... 514/211; 540/545
[58] Field of Search .............. 540/545; 514/211

*Primary Examiner*—Johann Richter
*Assistant Examiner*—Laura L. Stockton
*Attorney, Agent, or Firm*—Joseph J. Borovian

[57] ABSTRACT

The utility of known and novel staurosporin derivatives of formula I

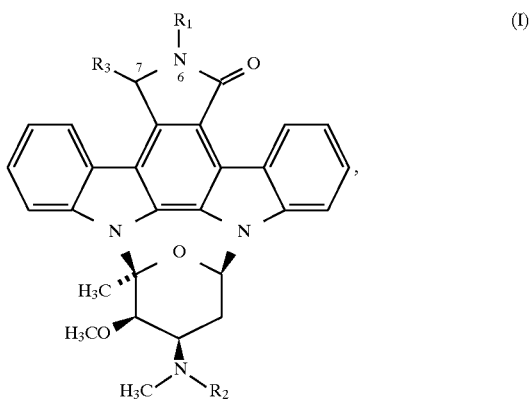

wherein
$R_1$ is formyl, an aliphatic hydrocarbon radical having up to 29 carbon atoms that is unsubstituted or substituted by aryl, or is an aryl radical,
$R_2$ is hydrogen, $C_1$–$C_5$alkyl, benzoyl, lower alkanoyl or α-aminoacyl having a free or protected amino group, and
$R_3$ is hydrogen, hydroxy, lower alkoxy or oxo,
or wherein
$R_1$ is methoxycarbonylmethyl,
$R_2$ is benzoyl, and
$R_3$ is hydrogen,
for avoiding or removing multi-drug resistance to antitumour agents, such as vinblastine or adriamycin, is described.

3 Claims, No Drawings

CARBAZOLE DERIVATIVES AS AGENTS AGAINST MULTI-DRUG RESISTANCE

This application is a 371 of PCT/EP 95/01909, filed May 19, 1995.

The invention relates to the use of known or novel staurosporin derivatives (indolocarbazole derivatives) for avoiding or removing multi-drug resistance to anti-tumour agents, to the novel derivatives as products, to a process for the preparation of the novel staurosporin derivatives and to pharmaceutical compositions comprising the novel derivatives.

Staurosporin, which forms the basis of the derivatives according to the invention, was isolated as early as 1977 from cultures of Streptomyces staurosporeus AWAYA, TAKAHASHI and OMURA, sp. nov. AM 2282, see S. Omura et al., J. Antibiot. 30, 275–281 (1977). Hitherto, only the relative, but not the absolute, configuration of staurosporin was known. The absolute configuration has been published only recently by N. Funato et al., Tetrahedron Letters 35:8, 1251–1254 (1994) and corresponds to the mirror image of the structure previously used in the literature to indicate the relative configuration of staurosporin. Accordingly, the Tetrahedron Letters publication recommends verbatim "that the stereochemical notation for staurosporine which has been in common use hitherto should be revised". Although the absolute configuration was not known hitherto, it was clearly established by the term "staurosporin derivative". In this text, the new formulae are used.

Staurosporin and most of the staurosporin derivatives known hitherto show a strong inhibitory action on protein kinase C. Protein kinase C, which is dependent upon phospholipids and calcium, occurs within the cell in several forms and participates in various fundamental processes, such as signal transmission, proliferation and differentiation and also secretion of hormones and neurotransmitters. Activation of that enzyme is brought about either by receptor-mediated hydrolysis of phospholipids of the cell membrane or by direct interaction with certain tumour-promoting active agents. The sensitivity of the cell towards receptor-mediated signal transmission can be significantly influenced by modifying the activity of protein kinase C (as the signal transmitter). Compounds that are capable of influencing the activity of protein kinase C may be used as tumour-inhibiting, anti-inflammatory, immuno-modulating and anti-bacterial active ingredients and may even be of interest as agents against atherosclerosis and disorders of the cardiovascular system and the central nervous system.

The inhibitory action on protein kinase C is weakened by a factor of from approximately 20 to over 1000 if the lactam nitrogen of staurosporin carries instead of hydrogen another substituent, that is to say, if the substituent $R_1$ in formula I shown hereinafter is other than hydrogen. Especially when in formula I below the radical $R_2$ is, at the same time, also other than hydrogen, the inhibitory action on protein kinase C is to all practical purposes lost. When the substituent $R_1$ in formula I shown below is other than hydrogen, the anti-tumour activity also decreases markedly. It is presumably for that reason that only few staurosporin derivatives wherein $R_1$ is other than hydrogen are described in the literature, although much work has been undertaken in the field in recent years and very many derivatives wherein $R_1$ is hydrogen have been prepared. Thus, the compound corresponding to formula I below wherein $R_1$ is benzyl, $R_2$ is benzoyl and $R_3$ is hydrogen, has mostly been mentioned only as a negative control.

The appearance of resistance to classical cytostatic agents is a great problem in cancer chemotherapy. The resistance is in many cases accompanied by a reduction in the intracellular concentration of active ingredient. That reduction is often associated with the appearance of a membrane-bound 170 kilodalton glycoprotein (Pgp). That protein acts as a pump having a broad specificity and is capable of transporting frequently used anti-tumour agents, such as the Vinca alkaloids, anthracyclins, podophyllotoxins and actinomycin D, out of the cell.

Surprisingly, it has now been found that staurosporin derivatives of formula I shown hereinbelow are capable of fully re-sensitising multidrug-resistant cells to the action of anti-tumour agents, such as cytostatics, as can be demonstrated inter alia by the example of resistant human KB-8511 cells. This is achieved even though, as mentioned above, all derivatives show a greatly weakened inhibitory action or no inhibitory action at all on protein kinase C and the anti-tumour activity is also markedly reduced. Also surprising is the high degree of sensitisation. In that respect, the staurosporin derivatives of formula I are roughly equivalent to the analogous derivatives wherein $R_1$ is hydrogen. Compared with a combination of a conventional cytostatic agent and a staurosporin derivative having pronounced anti-tumour activity and inhibitory action on protein kinase C, a combination of a conventional cytostatic agent with a staurosporin derivative of formula I shown hereinbelow has the advantage that the side-effects associated with the protein kinase C inhibitory action do not occur or occur only in a very much weaker form. The administration of protein kinase C inhibiting staurosporin derivatives results, for example in dogs, in nausea to the point of vomiting. The latter is understandably disadvantageous, especially for an orally administered anti-tumour agent, since active ingredient may also be vomited, with the result that the dose of active ingredient effectively taken may be different from the intended and administered dose.

The invention relates to the use of staurosporin derivatives of formula I

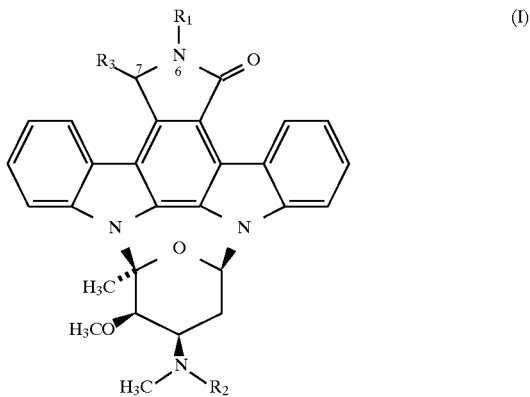

wherein
  $R_1$ is formyl, an aliphatic hydrocarbon radical having up to 29 carbon atoms that is unsubstituted or substituted by aryl, or is an aryl radical,
  $R_2$ is hydrogen, $C_1$–$C_5$alkyl, benzoyl, lower alkanoyl or α-aminoacyl having a free or protected amino group, and
  $R_3$ is hydrogen, hydroxy, lower alkoxy or oxo,
or wherein
  $R_1$ is methoxycarbonylmethyl,
  $R_2$ is benzoyl, and R₃ is hydrogen,
and of pharmaceutically acceptable salts of such compounds of formula I having at least one salt-forming group, for avoiding or removing multi-drug resistance to anti-tumour agents.

Unless stated otherwise, in this disclosure, organic radicals referred to as "lower" contain not more than 7, preferably not more than 4, carbon atoms.

An unsubstituted aliphatic hydrocarbon radical $R_1$ having up to 29 carbon atoms is an acyclic hydrocarbon radical having up to 29 carbon atoms, especially up to 18, and preferably up to 12, carbon atoms, and is saturated or unsaturated. Unsaturated radicals are those containing one or more, especially conjugated and/or isolated, multiple bonds (double and/or triple bonds). An unsubstituted aliphatic hydrocarbon radical is especially a linear or branched lower alkyl, lower alkenyl, lower alkadienyl or lower alkynyl radical. Lower alkyl is, for example, methyl, ethyl, n-propyl, isopropyl, n-butyl, isobutyl, sec-butyl or tert-butyl, or also n-pentyl, isopentyl, n-hexyl, isohexyl or n-heptyl; lower alkenyl is, for example, allyl, propenyl, isopropenyl, 2- or 3-methallyl or 2- or 3-butenyl; lower alkadienyl is, for example, 1-penta-2,4-dienyl; lower alkynyl is, for example, propargyl or 2-butynyl. In corresponding unsaturated radicals, the double bond is located especially in a position higher than the α-position with respect to the free valency.

An aliphatic hydrocarbon radical $R_1$ substituted by aryl is one in which an aliphatic hydrocarbon radical, especially one having a maximum of 7, preferably a maximum of 4, carbon atoms, such as especially methyl, ethyl and vinyl, carries one or more aryl radicals as defined below.

An aryl radical is especially a phenyl radical, but also a naphthyl radical, such as 1- or 2-naphthyl, a biphenylyl radical, such as especially 4-biphenylyl, or also an anthryl, fluorenyl or azulenyl radical, or an aromatic analogue thereof having one or more saturated rings. Preferred aryl-lower alkyl and aryl-lower alkenyl radicals are, for example, phenyl-lower alkyl or phenyl-lower alkenyl with a terminal phenyl radical, for example benzyl, phenethyl, 1-, 2- or 3-phenylpropyl, diphenylmethyl (benzhydryl), trityl and cinnamyl, and also 1- or 2-naphthylmethyl. Of the aryl radicals that carry acyclic radicals, such as lower alkyl, there are to be mentioned, in particular, o-, m- and p-tolyl and xylyl radicals having methyl radicals situated in different positions.

$C_1$–$C_5$alkyl $R_2$ is, for example, ethyl, n-propyl, n-butyl or, preferably, methyl.

Lower alkanoyl $R_2$ is, for example, acetyl.

$R_2$ as α-aminoacyl having a free amino group is an acyl radical derived from an α-amino acid, especially a naturally occurring α-amino acid of the L-series, such as glycine, phenylglycine, alanine, phenylalanine, proline, leucine, serine, valine, tyrosine, arginine, histidine or asparagine.

In $R_2$ as α-aminoacyl having a protected amino group, the amino group is protected by an amino-protecting group, especially by one of those mentioned hereinbelow, such as lower alkoxycarbonyl or benzyloxycarbonyl.

Lower alkoxy $R_3$ is preferably methoxy.

Depending on their nature, the compounds according to the invention may, provided they contain salt-forming groups, also be in the form of salts, especially pharmaceutically acceptable, i.e. physiologically tolerable, salts. For isolation or purification purposes it is also possible to use pharmaceutically unsuitable salts. Only pharmaceutically acceptable salts are used therapeutically and these are preferred.

Thus, compounds of formula I having free acid groups, such as a free sulfo, phosphoryl or carboxy group, may be in the form of a salt, preferably a physiologically tolerable salt, with a salt-forming basic component. There come into consideration especially metal or ammonium salts, such as alkali metal and alkaline earth metal salts, for example sodium, potassium, magnesium or calcium salts, or ammonium salts with ammonia or suitable organic amines, especially tertiary monoamines and heterocyclic bases, for example triethylamine, tri-(2-hydroxyethyl)-amine, N-ethylpiperidine or N,N'-dimethylpiperazine.

Compounds according to the invention of basic character may also be in the form of addition salts, especially in the form of acid addition salts with inorganic and organic acids, but also in the form of quaternary salts. Thus, for example, compounds of formula I that carry a basic group, such as an amino group, as a substituent may form acid addition salts with commonly used acids. Suitable acids are, for example, hydrohalic acids, for example hydrochloric and hydrobromic acid, sulfuric acid, phosphoric acid, nitric acid or perchloric acid, and aliphatic, alicyclic, aromatic or heterocyclic carboxylic or sulfonic acids, such as formic, acetic, propionic, succinic, glycolic, lactic, malic, tartaric, citric, fumaric, maleic, hydroxymaleic, oxalic, pyruvic, phenylacetic, benzoic, p-aminobenzoic, anthranilic, p-hydroxybenzoic, salicylic, p-aminosalicylic, embonic, methanesulfonic, ethanesulfonic, hydroxyethanesulfonic, ethylenedisulfonic, halobenzenesulfonic, toluenesulfonic, naphthalenesulfonic acids or sulfanilic acid, also methionine, tryptophan, lysine or arginine, or also ascorbic acid.

The staurosporin derivatives of formula I are capable of fully re-sensitising multidrug-resistant cells to the action of anti-tumour agents, such as cytostatics, as is demonstrated in the Examples section of this text in the case of resistant human KB-8511 cells. Such anti-tumour agents are, for example, doxorubicin, daunorubicin, vincristine, etoposide, taxol, mitomycin C, actinomycin D, mitozantrone and, especially, vinblastine and adriamycin. The staurosporin derivatives of formula I and pharmaceutically acceptable salts of such derivatives having at least one salt-forming group can therefore be used in combination with one of those anti-tumour agents for the treatment of tumour diseases.

As mentioned above, the inhibitory action of the compounds of formula I on protein kinase C virtually no longer exists or, compared with the analogous compounds wherein $R_1$ is hydrogen, is greatly weakened. To determine the protein kinase C inhibitory action, pig brain protein kinase C is used, which is purified in accordance with the procedure described by T. Uchida and C. R. Filburn in J. Biol. Chem. 259, 12311–4 (1984). The protein kinase C inhibitory action of the compounds of formula I was formerly determined according to the methodology of D. Fabbro et al., Arch. Biochem. Biophys. 239, 102–111 (1985). The pig brain protein kinase C used according to the methodology mentioned is a mixture of different subtypes (isotypes) of protein kinase C. For that reason, nowadays, pure, recombinant isotypes are mostly used instead of pig brain protein kinase C.

Recombinant PKC isotypes are cloned, expressed and purified as follows:

The preparation of various proteins with the aid of baculoviruses and their cloning and isolation from Sf9 insect cells is carried out as described by M. D. Summers and G. E. Smith, "A manual method for baculovirus vectors and insect cell culture procedure", Texas Agricul. Exptl. Station Bull. (1987), 1555. The construction and isolation of recombinant viruses for the expression of PKC-a (bovine), PKC- β1 (human), PKC-β2 (human) and PKC-γ (human/bovine hybrid) in Sf9 cells is carried out as described by Stabel et al., [S. Stabel, M. Liyanage and D. Frith, "Expression of protein kinase C isozymes in insect cells and isolation of recombinant proteins", Meth. Neurosc. (1993)]. The preparation of the PKC isotypes in Sf9 cells is carried out as specified by Stabel et al. (see above), and the purification of the enzymes is performed by the method described in the publication by McGlynn et al. [E. McGlynn, J. Liebetanz, S. Reutener, J. Wood, N. B. Lydon, H. Hofstetter, M. Vanek, T. Meyer and D. Fabbro, "Expression and partial characterization of rat protein kinase C-δ and protein kinase C-ζ in insect cells using recombinant baculovirus", J. Cell. Biochem. 49, 239–250 (1992)]. For the generation of recombinant PKC-δ (rat), PKC-ε (rat), PKC-ζ (rat) and PKC-η (mouse) and the expression and purification thereof the procedure described by Liyanage et al. ["Protein kinase C group B members PKC-δ, -ε, -ζ and PKC-λ: Comparison of properties of recombinant proteins in vitro and in vivo", Biochem. J. 283, 781–787 (1992)] and McGlynn et al. (see above) is followed, with the addition that, for the expression of PKC-η, the transfer vector pAc360 is used [V. Luckow and M. D. Summers, "Trends in the development of baculovirus expression", Biotechnology 6, 47–55 (1988)].

Measurement of the activity of the recombinant PKC isotypes obtained by the above method is carried out in the absence of lipid and calcium (co-factors). Protamine sulfate, which is phosphorylated in the absence of co-factors, is used as a substrate for this. The activity of the enzymes reflects the transfer of $^{32}P$ from γ-$[^{32}P]$-ATP to protamine sulfate. Protamine sulfate is a mixture of polypeptides that each comprise four C-terminal arginine residues. Measurement of the phosphate incorporation is carried out under the following conditions: 100 μl of the reaction mixture contain in final concentrations 20 mmol TRIS-HCl pH 7.4, 10 mmol Mg[NO$_3$]$_2$, 0.5 mg/ml protamine sulfate, 10 μmol ATP (0.1 μCi γ-$[^{32}P]$-ATP; 10 Ci/mol; Amersham, Little Chalfont, United Kingdom), various concentrations of inhibitory substances and 0.5–2.5 U (Units; one unit is the enzyme quantity that transfers one nanomol of 32P from the above-mentioned γ-$[^{32}P]$-ATP to Histon H1 [Sigma, type V-S] in one minute per milligram of protein) of the enzymes. The reaction is initiated by adding the enzymes and transferring to 32° C. The reaction time is 20 minutes. Thereafter, the reaction is stopped by dropping aliquots of 50 μl onto P81 chromatography paper (Whatman, Maidstone, United Kingdom). After removing unbound γ-$[^{32}P]$-ATP and nucleotide fractions by washing procedures as described by J. J. Witt and R. Roskoski, "Rapid protein kinase assay using phospho-cellulose-paper absorption", Anal. Biochem. 66, 253–258 (1975), the phosphorylation of the substrate is determined by scintillation measurement. In this test, the compounds of formula I generally do not inhibit the various isotypes of protein kinase C (PKC) until they are at a concentration IC$_{50}$ that is greater by a factor of from about 20 to over 1000 than the IC$_{50}$ values that are found for analogous compounds wherein R$_1$ is hydrogen.

Preference is given to the above-mentioned use of compounds of formula I wherein R$_1$ is an unsubstituted aliphatic hydrocarbon radical having up to 29 carbon atoms that is other than lower alkyl, or is an aliphatic hydrocarbon radical having up to 29 carbon atoms that is substituted by aryl, or is an aryl radical, and the other substituents are as defined above, and of pharmaceutically acceptable salts of such compounds of formula I having at least one salt-forming group.

Preference is given especially to the use of compounds of formula I wherein R$_1$ is lower alkyl, such as especially methyl, or benzyl, R$_2$ is hydrogen, benzoyl or α-aminoacyl selected from glycyl, phenylglycyl, alanyl, phenylalanyl, propyl, leucyl, seryl, valyl, tyrosyl, arginyl, histidyl and asparagyl, and R$_3$ is hydrogen or oxo, or wherein R$_1$ is methoxycarbonylmethyl, R$_2$ is benzoyl and R$_3$ is hydrogen, and of pharmaceutically acceptable salts of such compounds of formula I having at least one salt-forming group, for avoiding or removing multi-drug resistance to anti-tumour agents.

Especially preferred is the above-mentioned use of the compounds of formula I described in the Examples and of the pharmaceutically acceptable salts of such compounds of formula I having at least one salt-forming group.

The invention relates also to the compounds of formula I per se that do not belong to the prior art, i.e. compounds of formula I in the form of products wherein R$_1$ is an unsubstituted aliphatic hydrocarbon radical having from 6 to 29 carbon atoms, an aliphatic hydrocarbon radical having up to 29 carbon atoms that is substituted by aryl and is other than benzyl, or is an aryl radical, R$_2$ is hydrogen, C$_1$–C$_5$alkyl, lower alkanoyl or α-aminoacyl having a free or protected amino group, and R$_3$ is hydrogen, hydroxy, lower alkoxy or oxo, and salts of such compounds of formula I having at least one salt-forming group.

Preferred are compounds of formula I wherein R$_1$ is an unsubstituted aliphatic hydrocarbon radical having from 6 to 29 carbon atoms, an aliphatic hydrocarbon radical having up to 29 carbon atoms that is substituted by aryl and is other than benzyl, or is an aryl radical, R$_2$ is α-aminoacyl selected from glycyl, phenylglycyl, alanyl, phenylalanyl, prolyl, leucyl, seryl, valyl, tyrosyl, arginyl, histidyl and aspargyl, and R$_3$ is hydrogen or oxo, and salts of such compunds of formula I having at least one salt-forming group.

Especially preferred are compounds of formula I wherein R$_1$ is benzyl, R$_2$ is α-aminoacyl having a free or protected amino group, especially α-aminoacyl selected from glycyl, phenylglycyl, alanyl, phenylalanyl, prolyl, leucyl, seryl, valyl, tyrosyl, arginyl, histidyl and asparagyl, and R$_3$ is hydroxy, lower alkoxy, oxo or, preferably, hydrogen, and salts of such compounds of formula I having at least one salt-forming group.

Most preferred are those compounds of formula I mentioned in the Examples that are novel over the prior art, and the salts of such compounds of formula I having at least one salt-forming group.

The compounds of formula I and salts of such compounds having at least one salt-forming group are prepared by processes known per se. The process according to the invention comprises a) reacting a compound of formula II

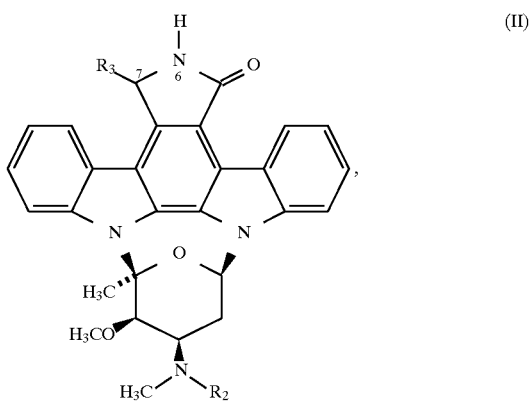

wherein the substituents are as defined above, any functional groups present in a compound of formula II being, if necessary, in protected form, or a salt of such a compound having at least one salt-forming group, with a compound of formula $$R_1Y \quad \text{(III)},$$

wherein $R_1$ is as defined above, any functional groups present therein being, if necessary, in protected form, and Y is a leaving group or an additional single bond the other end of which replaces a hydrogen atom in the radical $R_1$, or with a salt of such a compound having at least one salt-forming group, and removing any protecting groups, or b) reacting a compound of formula IV

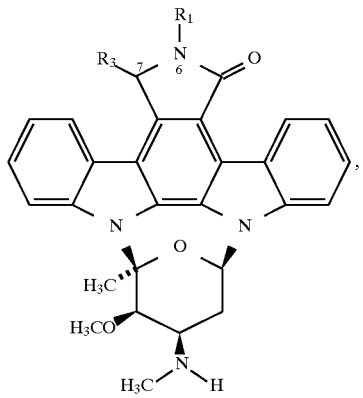

wherein the substituents are as defined above, any functional groups present therein being, if necessary, in protected form, or a salt of such a compound having at least one salt-forming group, with a compound of formula $$R_2{}^aX \quad \text{(V)},$$

wherein $R_2{}^a$ has the above-mentioned meanings of $R_2$ with the exception of hydrogen, any functional groups present in the radical $R_2{}^a$ being, if necessary, in protected form, and X is a leaving group or an additional single bond the other end of which replaces a hydrogen atom in the radical $R_2{}^a$, or with a salt of such a compound having at least one salt-forming group, and removing any protecting groups, and, if desired, converting a resulting compound of formula I into a different compound of formula I and/or converting a compound of formula I obtained in free form into a salt thereof and/or converting a compound of formula I obtained in the form of a salt into its free form or into a different salt.

The way in which the above-mentioned process variants are carried out is explained in detail below:

General remarks

The end products of formula I may contain substituents that can also be used as protecting groups in starting materials for the preparation of other end products of formula I. Within the scope of this text, therefore, unless otherwise apparent from the context, the term "protecting group" denotes only a readily removable group that is not a component part of the particular desired end product of formula I.

Process a)

Free functional groups that may be present in compounds of formulae II and III, which are preferably protected by readily removable protecting groups, are especially free amino or carboxy groups. It may also be advantageous to protect free hydroxy. Functional groups that are intended to participate in the desired reaction are not, of course, protected.

Protecting groups and the methods by which they are introduced and removed are described, for example, in "Protective Groups in Organic Chemistry", Plenum Press, London, New York 1973, and in "Methoden der organischen Chemie", Houben-Weyl, 4th edition, Vol. 15/1, Georg-Thieme-Verlag, Stuttgart 1974 and also in Theodora W. Greene, "Protective Groups in Organic Synthesis", John Wiley & Sons, New York 1981. It is characteristic of protecting groups that they can be removed easily, i.e. without undesirable secondary reactions taking place, for example by solvolysis, reduction, photolysis or also under physiological conditions.

A protected amino group may, for example, be in the form of a readily cleavable acylamino, arylmethylamino, etherified mercaptoamino, 2-acyl-lower alk-1-en-yl-amino, silylamino or stannylamino group or in the form of an azido group.

In a corresponding acylamino group, acyl is, for example, the acyl radical of an organic carboxylic acid having, for example, up to 18 carbon atoms, especially of an unsubstituted or substituted, for example halo- or aryl-substituted, alkanecarboxylic acid or an unsubstituted or substituted, for example halo-, lower alkoxy- or nitro-substituted, benzoic acid, or of a carbonic acid semiester. Such acyl groups are, for example, lower alkanoyl, such as formyl, acetyl or propionyl, halo-lower alkanoyl, such as 2-haloacetyl, especially 2-chloro-, 2-bromo-, 2-iodo-, 2,2,2-trifluoro- or 2,2, 2-trichloro-acetyl, unsubstituted or substituted, for example halo-, lower alkoxy- or nitro-substituted, benzoyl, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, especially tert-lower alkoxycarbonyl, for example tert-butoxycarbonyl, arylmethoxycarbonyl having one or two aryl radicals which are preferably phenyl that is unsubstituted or is mono- or poly-substituted, for example, by lower alkyl, especially tert-lower alkyl, such as tert-butyl, lower alkoxy, such as methoxy, hydroxy, halogen, for example chlorine, and/or by nitro, such as unsubstituted or substituted benzyloxycarbonyl, for example 4-nitrobenzyloxycarbonyl, or substituted diphenylmethoxycarbonyl, for example benzhydryloxycarbonyl or di-(4-methoxyphenyl)-methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(trisubstituted silyl)-ethoxycarbonyl wherein each substituent independently is an aliphatic, araliphatic, cycloaliphatic or aromatic hydrocarbon radical having up to 15 carbon atoms that is unsubstituted or substituted, for example, by lower alkyl, lower alkoxy, aryl, halogen or by nitro, such as corresponding, unsubstituted or substituted, lower alkyl, phenyl-lower alkyl, cycloalkyl or phenyl, for example 2-tri-lower alkylsilylethoxycarbonyl, such as 2-trimethylsilylethoxycarbonyl or 2-(di-n-butyl-methyl-silyl)-ethoxycarbonyl, or 2-triarylsilylethoxycarbonyl, such as 2-triphenylsilylethoxycarbonyl.

Other acyl radicals that are suitable as amino-protecting groups are also corresponding radicals of organic phosphoric, phosphonic or phosphinic acids, such as di-lower alkylphosphoryl, for example dimethylphosphoryl, diethylphosphoryl, di-n-propylphosphoryl or diisopropylphosphoryl, dicycloalkylphosphoryl, for example dicyclohexylphosphoryl, unsubstituted or substituted diphenylphosphoryl, for example diphenylphosphoryl, unsubstituted or substituted, for example nitro-substituted, di-(phenyl-lower alkyl)-phosphoryl, for example dibenzylphosphoryl or di-(4-nitrobenzyl)-phosphoryl, unsubstituted or substituted phenyloxy-phenyl-phosphonyl, for example phenyloxyphenyl-phosphonyl, di-lower alkylphosphinyl, for example diethylphosphinyl, or unsubstituted or substituted diphenylphosphinyl, for example diphenylphosphinyl.

In an arylmethylamino group that is a mono-, di- or, especially, a tri-arylmethylamino group, the aryl radicals are, especially, unsubstituted or substituted phenyl radicals. Such groups are, for example, benzyl-, diphenylmethyl- and, especially, trityl-amino.

An etherified mercapto group in an amino group protected by such a radical is especially arylthio or aryl-lower alkylthio wherein aryl is especially phenyl that is unsubstituted or substituted, for example, by lower alkyl, such as methyl or tert-butyl, lower alkoxy, such as methoxy, halogen, such as chlorine, and/or by nitro. A corresponding aminoprotecting group is, for example, 4-nitrophenylthio.

In a 2-acyl-lower alk-1-en-1-yl radical that can be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-prop-1-en-2-yl, for example 1-acetyl-prop-1-en-2-yl, or 1-lower alkoxycarbonyl-prop-1-en-2-yl, for example 1-ethoxycarbonyl-prop-1-en-2-yl.

Preferred amino-protecting groups are acyl radicals of carbonic acid semiesters, especially tert-butoxycarbonyl, benzyloxycarbonyl that is unsubstituted or substituted, for example as indicated, for example 4-nitrobenzyloxycarbonyl, or diphenylmethoxycarbonyl, or 2-halo-lower alkoxycarbonyl, such as 2,2,2-trichloroethoxycarbonyl, also trityl or formyl. Carboxy groups are usually protected in esterified form, such ester groupings being readily cleavable under mild conditions. Carboxy groups protected in that manner contain as esterifying groups especially lower alkyl groups that are branched in the 1-position or suitably substituted in the 1- or 2-position. Preferred carboxy groups in esterified form are inter alia tert-lower alkoxycarbonyl, for example tert-butoxycarbonyl, arylmethoxycarbonyl having one or two aryl radicals which are phenyl radicals that are unsubstituted or mono- or poly-substituted, for example, by lower alkyl, such as tert-lower alkyl, for example tert-butyl, lower alkoxy, such as methoxy, hydroxy, halogen, for example chlorine, and/or by nitro, such as benzyloxycarbonyl that is unsubstituted or substituted, for example as mentioned above, for example 4-methoxybenzyloxycarbonyl or 4-nitrobenzyloxycarbonyl, or diphenylmethoxycarbonyl that is unsubstituted or substituted, for example as mentioned above, for example diphenylmethoxycarbonyl or di-(4-methoxyphenyl)-methoxycarbonyl, -lower alkoxy-lower alkoxycarbonyl, such as methoxymethoxycarbonyl, 1-methoxyethoxycarbonyl or 1-ethoxymethoxycarbonyl, -lower alkylthio-lower alkoxycarbonyl, such as 1-methylthiomethoxycarbonyl or 1-ethylthioethoxycarbonyl, aroylmethoxycarbonyl wherein the aroyl group is benzoyl that is unsubstituted or substituted, for example by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(trisubstituted silyl)ethoxycarbonyl wherein each substituent independently is an aliphatic, araliphatic, cycloaliphatic or aromatic hydrocarbon radical that is unsubstituted or substituted, for example, by lower alkyl, lower alkoxy, aryl, halogen and/or by nitro, such as corresponding, unsubstituted or substituted, lower alkyl, phenyl-lower alkyl, cycloalkyl or phenyl, for example 2-tri-lower alkylsilylethoxycarbonyl, 2-trimethylsilylethoxycarbonyl or 2-(di-n-butyl-methyl-silyl)ethoxycarbonyl, or 2-triarylsilylethoxycarbonyl, such as 2-triphenylsilylethoxycarbonyl.

The organic silyl and stannyl radicals mentioned above and hereinafter contain preferably lower alkyl, especially methyl, as substituents of the silicon or tin atoms. Corresponding silyl or stannyl groups are especially tri-lower alkylsilyl, especially trimethylsilyl, or dimethyl-tert-butyl-silyl, or correspondingly substituted stannyl, for example tri-n-butylstannyl.

Preferred protected carboxy groups are tert-lower alkoxycarbonyl, such as tert-butoxycarbonyl, and especially benzyloxycarbonyl that is unsubstituted or substituted, for example as mentioned above, such as 4-nitrobenzyloxycarbonyl, or diphenylmethoxycarbonyl, especially 2-(trimethylsilyl)ethoxycarbonyl.

Hydroxy-protecting groups are, for example, acyl radicals, such as unsubstituted or substituted, for example halo-substituted, lower alkanoyl, such as 2,2-dichloroacetyl, or acyl radicals of carbonic acid semiesters, especially tert-butoxycarbonyl, unsubstituted or substituted benzyloxycarbonyl, for example 4-nitrobenzyloxycarbonyl, or diphenylmethoxycarbonyl, or 2-halo-lower alkoxycarbonyl, such as 2,2,2-trichloroethoxycarbonyl, also trityl or formyl, or organic silyl or stannyl radicals, or readily removable etherifying groups, such as tert-lower alkyl, for example tert-butyl, 2-oxa- or 2-thia-aliphatic or -cycloaliphatic hydrocarbon radicals, especially -lower alkoxy-lower alkyl or -lower alkylthio-lower alkyl, for example methoxymethyl, 1-methoxy-ethyl, 1-ethoxy-ethyl, methylthiomethyl, 1-methylthioethyl or 1-ethylthioethyl, or 2-oxa- or 2-thia-cycloalkyl having 5 or 6 ring atoms, for example tetrahydrofuryl or 2-tetrahydropyranyl or corresponding thia analogues, and also unsubstituted or substituted 1-phenyl-lower alkyl, such as unsubstituted or substituted benzyl or diphenylmethyl, suitable substituents of the phenyl radicals being, for example, halogen, such as chlorine, lower alkoxy, such as methoxy, and/or nitro.

The removal of protecting groups that are not constituents of the desired end product of formula I, for example the carboxy-, amino-, hydroxy- or carbamoyl-protecting groups, is effected in a manner known per se, for example by means of solvolysis, especially hydrolysis, alcoholysis or acidolysis, or by means of reduction, especially hydrogenolysis or chemical reduction, as appropriate stepwise or simultaneously, it being possible also to use enzymatic methods, for example acidolysis, such as treatment with trifluoroacetic acid or formic acid, or reduction, such as treatment with zinc and acetic acid, or with hydrogen and a hydrogenation catalyst, such as a palladium-on-carbon catalyst.

When several protected functional groups are present, the protecting groups are preferably so chosen that more than one such group can be removed simultaneously.

A protected amino group is freed in a manner known per se and, according to the nature of the protecting groups, in various ways, preferably by solvolysis or reduction. 2-Halolower alkoxycarbonylamino (where appropriate after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxylic acid, such as aqueous acetic acid. Aroylmethoxycarbonylamino can be cleaved also by treatment with a nucleophilic, preferably salt-forming, reagent, such as sodium thiophenolate, and 4-nitrobenzyloxycarbonylamino also by treatment with an alkali metal dithionite, for example sodium dithionite. Unsubstituted or substituted diphenylmethoxycarbonylamino, tert-lower alkoxycarbonylamino or 2-tri-substituted silylethoxycarbonylamino, can be cleaved by treatment with a suitable acid, for example formic acid or trifluoroacetic acid, or with hydrochloric acid in ethyl acetate or dioxane; unsubstituted or substituted benzyloxycarbonylamino can be cleaved, for example, by means of hydrogenolysis, i.e. by treatment with hydrogen in the presence of a suitable hydrogenation catalyst, such as a palladium catalyst; unsubstituted or substituted triarylmethylamino or formylamino can be cleaved, for example, by treatment with an acid, such as a mineral acid, for example hydrochloric acid, or an organic acid, for example formic, acetic or trifluoroacetic acid, where appropriate in the presence of water; and an amino group protected by an organic silyl group can be freed, for example, by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate, of thiourea, and subsequent solvolysis, such as alcoholysis or hydrolysis, of the resulting condensation product. An amino group protected by 2-substituted silylethoxycarbonyl can be converted into the free amino group also by treatment with a salt of hydrofluoric acid that yields fluoride anions.

Tert-lower alkoxycarbonyl, lower alkoxycarbonyl substituted in the 2-position by an organic silyl group or in the 1-position by lower alkoxy or by lower alkylthio, or unsubstituted or substituted diphenylmethoxycarbonyl can be converted into free carboxy, for example, by treatment with a suitable acid, such as formic acid or trifluoroacetic acid, where appropriate with the addition of a nucleophilic compound, such as phenol or anisole. Unsubstituted or substituted benzyloxycarbonyl can be freed, for example, by means of hydrogenolysis, i.e. by treatment with hydrogen in the presence of a metal hydrogenation catalyst, such as a palladium catalyst. In addition, suitably substituted benzyloxycarbonyl, such as 4-nitrobenzyloxycarbonyl, can be converted into free carboxy also by chemical reduction, for example by treatment with an alkali metal dithionite, such as sodium dithionite, or with a reducing metal, for example zinc, or a reducing metal salt, such as a chromium (II) salt, for example chromium(II) chloride, customarily in the presence of a hydrogen-yielding agent that, together with the metal, is capable of producing nascent hydrogen, such as an acid, especially a suitable carboxylic acid, such as an unsubstituted or substituted, for example hydroxy-substituted, lower alkanecarboxylic acid, for example acetic acid, formic acid, glycolic acid, diphenylglycolic acid, lactic acid, mandelic acid, 4-chloromandelic acid or tartaric acid, or in the presence of an alcohol or thiol, water preferably being added. By treatment with a reducing metal or metal salt, as described above, 2-halo-lower alkoxycarbonyl (where appropriate after conversion of a 2-bromo-lower alkoxycarbonyl group into a corresponding 2-iodo-lower alkoxycarbonyl group) or aroylmethoxycarbonyl can also be converted into free carboxy. Aroylmethoxycarbonyl can be cleaved also by treatment with a nucleophilic, preferably salt-forming, reagent, such as sodium thiophenolate or sodium iodide. Substituted 2-silylethoxycarbonyl can also be converted into free carboxy by treatment with a salt of hydrofluoric acid that yields the fluoride anion, such as an alkali metal fluoride, for example sodium or potassium fluoride, in the presence of a macrocyclic polyether ("crown ether"), or with a fluoride of an organic quaternary base, such as tetra-lower alkylammonium fluoride or tri-lower alkyl-arylammonium fluoride, for example tetraethylammonium fluoride or tetrabutylammonium fluoride, in the presence of an aprotic, polar solvent, such as dimethyl sulfoxide or N,N-dimethylacetamide.

A hydroxy group protected by a suitable acyl group, an organic silyl group or by unsubstituted or substituted 1-phenyl-lower alkyl is freed analogously to a correspondingly protected amino group. Hydroxy protected by unsubstituted or substituted 1-phenyl-lower alkyl, for example benzyl, is freed preferably by catalytic hydrogenation, for example in the presence of a palladium-on-carbon catalyst. A hydroxy group protected by 2,2-dichloroacetyl is freed, for example, by basic hydrolysis, and a hydroxy group etherified by tert-lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid. Hydroxy etherified by an organic silyl radical, for example trimethylsilyl, can also be freed with a salt of hydrofluoric acid that yields fluoride anions, for example tetrabutylammonium fluoride.

If Y is a leaving group that is bonded to a non-aromatic carbon atom in the radical $R_1$, Y is especially a reactive esterified hydroxy group, i.e. one that is esterified by a strong inorganic acid, such as a hydrohalic acid (for example hydrochloric, hydrobromic or hydriodic acid), by an oxygen-containing mineral acid, such as phosphoric acid and, especially, sulfuric acid, or by a strong organic, such as aliphatic or aromatic, sulfonic acid (for example methane- and ethane- or benzene-, p-toluene-, p-nitrobenzene- and p-chlorobenzene-sulfonic acid).

If Y is a leaving group that is bonded to an aromatic carbon atom in the radical $R_1$, for example to a phenyl radical, Y is especially a diazonium group.

If Y is an additional single bond the other end of which replaces a hydrogen atom in the radical $R_1$, $R_1Y$ is, for example, an alkene, especially one in which the double bond has been additionally activated by a structural peculiarity, as in 2-methylpropene, or by substitution, such as especially in acrylonitrile. Also included in the definition of Y is a single bond the other end of which is not bonded directly to a carbon atom in the radical $R_1$ but is bonded to a hetero atom occurring as a substituent, such as oxygen (for example in a hydroxy group) or nitrogen (in an amino group) (replacing a hydrogen atom of that group). Especially preferred reagents of that kind contain the α-epoxide (oxirane) or α-imine (aziridine) grouping and serve as an advantageous source of radicals R° having a 2-hydroxyalkyl grouping or 2-aminoalkyl grouping, respectively.

If $R_1$ is formyl, the reagent $R_1Y$ is a reactive carboxylic acid derivative. Y therein is, for example, a reactive esterified hydroxy group, such as especially halogen. Such reactive carboxylic acid derivatives of formula III are especially reactive activated esters or reactive anhydrides, or also reactive cyclic amides, it also being possible for the activation of the carboxylic acid of formula $R_1$—OH used as acylating agent to be performed in situ in the presence of the compound of formula II.

Activated esters of acids are especially esters that are unsaturated at the linking carbon atom of the esterifying radical, for example of the vinyl ester type, such as vinyl esters proper (obtainable, for example, by transesterification of a corresponding ester with vinyl acetate; activated vinyl ester method), carbamoylvinyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-disubstituted carbodiimide, for example N,N'-dicyclohexylcarbodiimide; carbodiimide method), or N,N-disubstituted amidino esters (obtainable, for example, by treatment of the corresponding acid with an N,N-disubstituted cyanamide; cyanamide method), suitable aryl esters, especially phenyl esters suitably substituted by electron-attracting substituents (obtainable, for example, by treatment of the corresponding acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl esters method), cyanomethyl esters (obtainable, for example, by treatment of the corresponding acid with chloroacetonitrile in the presence of a base; cyanomethyl esters method), thioesters, especially unsubstituted or substituted, for example nitro-substituted, phenylthio esters (obtainable, for example, by treatment of the corresponding acid with unsubstituted or substituted, for example nitro-substituted, thiophenols, inter alia by the anhydride or carbodiimide method; activated thiol esters method), amino or amido esters (obtainable, for example, by treatment of the corresponding acid with an N-hydroxyamino or N-hydroxyamido compound, for example N-hydroxysuccinimide, N-hydroxypiperidine, N-hydroxyphthalimide or 1-hydroxybenzotriazole, for example by the anhydride or carbodiimide method; activated N-hydroxy esters method), or silyl esters (which are obtainable, for example, by treatment of the corresponding acid with a silylating agent, for example hexamethyldisilazane, and which readily react with hydroxy groups but not with amino groups).

Anhydrides of acids may be symmetric or preferably mixed anhydrides of those acids, for example anhydrides with inorganic acids, such as acid halides, especially acid chlorides (obtainable, for example, by treatment of the corresponding acid with thionyl chloride, phosphorus pentachloride or oxalyl chloride; acid chloride method), azides (obtainable, for example, from a corresponding acid ester via the corresponding hydrazide and treatment thereof with nitrous acid; azide method), anhydrides with carbonic acid semiderivatives, such as corresponding esters, for example carbonic acid lower alkyl semiesters (obtainable, for example, by treatment of the corresponding acid with haloformic, such as chloroformic, acid lower alkyl esters or with a 1-lower alkoxycarbonyl-2-lower alkoxy-1,2-dihydroquinoline, for example 1-lower alkoxycarbonyl-2-ethoxy-1,2-dihydroquinoline; mixed O-alkylcarbonic acid anhydrides method), or anhydrides with dihalogenated, especially dichlorinated, phosphoric acid (obtainable, for example, by treatment of the corresponding acid with phosphorus oxychloride; phosphorus oxychloride method), or anhydrides with organic acids, such as mixed anhydrides with organic carboxylic acids (obtainable, for example, by treatment of the corresponding acid with an unsubstituted or substituted lower alkane- or phenyl-alkanecarboxylic acid halide, for example phenylacetic acid chloride, pivalic acid chloride or trifluoroacetic acid chloride; mixed carboxylic acid anhydrides method) or with organic sulfonic acids (obtainable, for example, by treatment of a salt, such as an alkali metal salt, of the corresponding acid with a suitable organic sulfonic acid halide, such as a lower alkane- or aryl-, for example methane- or p-toluene-sulfonic acid chloride; mixed sulfonic acid anhydrides method) and symmetric anhydrides (obtainable, for example, by condensation of the corresponding acid in the presence of a carbodiimide or 1-diethylaminopropyne; symmetric anhydrides method).

Suitable cyclic amides are especially amides having five-membered diazacycles of aromatic character, such as amides with imidazoles, for example imidazole (obtainable, for example, by treatment of the corresponding acid with N,N'-carbonyldiimidazole; imidazolide method), or pyrazoles, for example 3,5-dimethylpyrazole (obtainable, for example, via the acid hydrazide by treatment with acetylacetone; pyrazolide method).

As mentioned, derivatives of acids used as acylating agents can also be formed in situ. Thus, for example, N,N'-disubstituted amidino esters can be formed in situ by reacting a mixture of the starting material of formula II and the acid used as acylating agent in the presence of a suitable N,N-disubstituted carbodiimide, for example N,N'-dicyclohexylcarbodiimide. It is also possible to form amino or amido esters of the acids used as acylating agents in the presence of the starting material of formula II that is to be acylated, by reacting a mixture of the corresponding acid and amino starting materials in the presence of an N,N'-disubstituted carbodiimide, for example N,N'-dicyclohexylcarbodiimide, and of an N-hydroxyamine or N-hydroxyamide, for example N-hydroxysuccinimide, N-hydroxy-norbomane-2,3-dicarboximide or N-hydroxybenzotriazole, where appropriate in the presence of a suitable base, for example 4-dimethylaminopyridine or tetramethylguanidine.

In order to introduce a radical $R_1$ that is other than acyl (formyl), Process a) is preferably carried out by first reacting the starting material of formula II in a suitable solvent, such as dimethylformamide or tetrahydrofuran, with a suitable base, such as sodium bis(trimethylsilyl)amide in tetrahydrofuran or sodium hydride, at a temperature of preferably from −20° C. to +70° C., especially from 0° C. to room temperature, and then adding the compound of formula III, for example in a suitable solvent, such as tetrahydrofuran. In order to introduce an acyl radical (formyl radical) $R_1$, Process a) is preferably carried out by reacting the starting material of formula II in a suitable solvent, such as methylene chloride, in the presence of a suitable base, such as triethylamine, with a reactive acid derivative of formula III, which may also be formed in situ from the corresponding acid, at a temperature of from 0° C. to +150° C., for example under reflux. Alternatively, the starting material of formula II can first be reacted in a suitable solvent, such as absolute tetrahydrofuran, with a suitable base, such as sodium bis (trimethylsilyl)amide in tetrahydrofuran, at a temperature of from 0° C. to room temperature, and then a reactive acid derivative of formula III can be added.

Process b)

The functional groups to be protected in the reactants of formulae IV and V and the protecting groups used for that purpose correspond to those mentioned in Process a). Functional groups that are intended to participate in the desired reaction, such as the group —NH—CH$_3$, are not, of course, protected. The introduction and removal of the protecting groups is also carried out analogously to the manner described in Process a). In the case of non-aromatic radicals $R_2$, the leaving group X in a compound of formula V corresponds to the reactive activated hydroxy group Y in the compound of formula III and the reagents of formula V are analogous to the reagents of formula III. In the case of aromatic radicals $R_2$, the leaving group X is, for example, a diazonium group.

In order to introduce a radical $R_2{}^a$ that is other than acyl, Process b) is preferably carried out by reacting the starting material of formula IV in a suitable solvent, such as dimethylformamide or a halogenated hydrocarbon, such as chloroform, in the presence of a suitable base, such as N,N-diisopropylethylamine, at a suitable temperature, such as room temperature or elevated temperature up to about +150° C., with a compound of formula V, the reaction being carried out at elevated temperature, for example under pressure in a closed vessel, such as a bomb tube, especially when X is an additional single bond the other end of which replaces a hydrogen atom in the radical $R_2$, for example when the compound of formula V is an oxirane or acrylonitrile. The reaction with oxiranes is preferably carried out in a lower alkanol, such as ethanol, as solvent.

In order to convert a compound of formula I obtained by Process a) or b) into a different compound of formula I, for example an ester grouping can be hydrolysed to carboxy or a carbonyl group can be reduced. The said hydrolysis is carried out, for example, in a manner known per se with dilute, for example 2-normal, sodium hydroxide solution in a lower alkanol, such as ethanol, at room temperature, and can also be seen as the removal of a protecting group. For the reduction of a carbonyl group, including a carbonyl group forming part of an amide or lactam group, reducing agents that come into consideration are, for example, complex metal hydrides, such as alkali metal aluminium hydrides and, especially, alkali metal borohydrides, for example lithium aluminium hydride, potassium borohydride, lithium borohydride and, especially, sodium borohydride, and derivatives thereof wherein one or more hydrogen atoms have been replaced by alkoxy radicals or by cyano, for example methoxysodium borohydride, tri-(tert-butoxy)lithium borohydride or di-(2-methoxyethoxy)-disodium lithium hydride or sodium cyanoborohydride, and also diborane.

Salt-forming groups in compounds of formulae II to V and salts thereof are those mentioned above for the compounds of formula I.

The salt formation, which is to be carried out if desired, or the freeing of the fundamental forms from their salts is carried out in a conventional manner that is generally known per se. Thus, compounds carrying carboxy groups are converted into corresponding salts with bases, especially into alkali metal salts, by treatment with a corresponding base, especially a compound giving an alkaline reaction, such as a hydroxide, carbonate or bicarbonate. The salts can be converted into free carboxy compounds by acidifying, for example with inorganic acids, such as especially hydrohalic acids. End products giving a basic reaction, for example amines, can be converted into their salts with acids, for example by treatment with an acid suitable for salt formation, such as one of those mentioned above; conversely, by treating with agents that give a basic reaction, such as with inorganic hydroxides, carbonates and bicarbonates, or organic bases and ion-exchangers, such a basic fundamental form of an amine is freed.

Salts, such as the picrates, can also be used for the purification of the compounds obtained, by converting the free compounds into salts, separating these and recovering the free compounds from the salts again.

In view of the close relationship between the compounds in free form and in the form of their salts, hereinbefore and hereinafter any reference to the free compounds is to be understood as including also the corresponding salts (including quaternary salts) where appropriate and expedient.

The starting materials corresponding to the formula IV wherein, however, $R_1$ is hydrogen are known or can be prepared by processes that are known per se. The starting material corresponding to the formula IV wherein $R_1$ and $R_3$ are each hydrogen, i.e. staurosporin, is commercially available and can be obtained by fermentation with the strain *Streptomyces staurosporeus*. That strain was deposited under number FERM P-3725 at the Fermentation Research Institute, Japan, in connection with Japanese Examined Patent Publication [Kokoku] No. 57-53076 which was published on 11 Nov. 1982, see S. Omura et al., J. Antibiot. 30, 275–281 (1977). Staurosporin derivatives corresponding to formula IV wherein $R_3$ is other than hydrogen are, for example, described by I. Takahashi et al., J. Pharmacol. Exp. Ther. 255(3) (1990) 1218–1221 and in WO-A-8907-105-A (Applicant: Kyowa Hakko Kogyo KK, Japanese Priority No. 024571 of Apr. 2, 1988). Compounds of formula II wherein $R_3$ is oxo are obtained, for example, from the corresponding compounds of formula II wherein $R_3$ is hydrogen by oxidation with chromium trioxide in pyridine. From the 7-oxo compounds so obtained the corresponding 7-hydroxy compounds wherein $R_3$ is hydroxy are obtained by reduction with sodium borohydride. Compounds corresponding to formula I wherein $R_3$ is hydroxy or oxo are also obtained as a by-product in the synthesis of compounds of formula I wherein $R_3$ is hydrogen. From the known staurosporin derivatives the starting materials of formulae II and IV that are still novel are obtained by appropriately carrying out reactions that are analogous to Process variants a) and b) described above.

Unless stated otherwise, all of the processes described above, including the processes for removing protecting groups and the additional process measures, are carried out in a manner known per se, for example in the presence or absence of preferably inert solvents and diluents, if necessary in the presence of condensation agents or catalysts, at reduced or elevated temperature, for example in a temperature range of from approximately −70° C. to approximately +150° C., especially from approximately −20° C. to approximately +100° C., mainly from approximately 0° C. to approximately +70° C., preferably from approximately 0° C. to approximately +50° C., mainly at room temperature, in a suitable vessel and, if necessary, under an inert gas atmosphere, for example a nitrogen atmosphere.

In those processes, taking into consideration all of the substituents in the molecule, if necessary, for example if readily hydrolysable radicals are present, especially mild reaction conditions are to be used, such as short reaction times, the use of mild acidic or basic agents in low concentration, stoichiometric quantity ratios, selection of suitable catalysts, solvents and temperature and/or pressure conditions.

The invention relates also to those forms of the process in which a compound obtainable as intermediate at any stage of the process is used as starting material and the remaining steps are carried out, or the process is discontinued at any stage or a starting material is formed under the reaction conditions or is used in the form of a reactive derivative or salt. The starting materials used are preferably those which result in accordance with the process in the compounds described above as being especially valuable.

The present invention relates also to novel starting materials and/or intermediates and to processes for the preparation thereof. The starting materials used and the reaction conditions chosen are preferably such that the compounds mentioned in this Application as being especially preferred are obtained.

The invention relates also to the use of the compounds of formula I and their pharmaceutically acceptable acid addition salts, preferably in the form of pharmaceutical compositions, for the therapeutic treatment of the human or animal body, especially in the case of the diseases mentioned above. The invention relates also to a method of removing existing multi-drug resistance and of preventing the development of multi-drug resistance in a warm-blooded animal in need of such treatment, wherein an effective dose that removes the multi-drug resistance and avoids the development thereof of a compound of formula I, or of a pharmaceutically acceptable salt thereof, is administered enterally, for example orally, or parenterally, for example intraperitoneally or intravenously, to that warm-blooded animal. The dose of the active ingredient depends inter alia upon the nature of the disease, the species to be treated and its size, the organism's state of defence and the mode of administration. For example, a daily dose of from 10 mg to 1000 mg, mainly from 50 mg to 500 mg, preferably from 70 mg to 300 mg, for example 150 mg, of a compound of formula I will be administered enterally or parenterally, for example intraperitoneally, to a warm-blooded animal of approximately 70 kg body weight. This total daily dose may be divided into 2 or 3 doses per day.

The invention relates also to pharmaceutical compositions that comprise an effective amount, especially an amount effective for the prophylaxis or treatment of one of the diseases mentioned above, of the active ingredient together with pharmaceutically acceptable carriers that are suitable for topical, enteral, for example oral or rectal, or parenteral, for example intravenous or intraperitoneal, administration, and may be inorganic or organic and solid or liquid. For oral administration there are used especially tablets or gelatin capsules that comprise the active ingredient together with diluents, for example lactose, dextrose, sucrose, mannitol, sorbitol, cellulose and/or glycerol, and/or lubricants, for example silica, talc, stearic acid or salts thereof, such as magnesium or calcium stearate, and/or polyethylene glycol. Tablets may also comprise binders, for example magnesium aluminium silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, colourings, flavourings and sweeteners. It is also possible to use the pharmacologically active compounds of the present invention in the form of parenterally administrable compositions or infusion solutions. Such solutions are preferably isotonic aqueous solutions or suspensions, it being possible, for example in the case of lyophilised compositions that comprise the active ingredient on its own or together with a carrier, for example mannitol, for such solutions or suspensions to be made up prior to use. The pharmaceutical compositions may be sterilised and/or may comprise excipients, for example preservatives, stabilisers, wetting agents and/or emulsifiers, solubilisers, salts for regulating the osmotic pressure and/or buffers. The pharmaceutical compositions in question, which may, if desired, comprise other pharmacologically active substances, such as antibiotics, are prepared in a manner known per se, for example by means of conventional mixing, granulating, confectioning, dissolving or lyophilising processes, and comprise approximately from 0.01% to 90%, and in the case of lyophilised compositions up to 100%, especially from approximately 0.1% to approximately 50%, most especially from 1% to 30%, active ingredient(s), an active ingredient concentration below 1% being especially suitable for compositions for topical administration.

The following Examples illustrate the invention without limiting it in any way. The $R_f$ values are determined on silica gel thin-layer plates (produced by Merck, Darmstadt, Germany). The ratio of the eluants to one another in the eluant mixtures used is given in parts by volume (v/v), and temperatures are given in degrees Celsius. In the case of optical rotation, the concentration, c, of the substance in the solvent or solvent mixture is given as a percentage (weight/volume).

Within the scope of this text, the following nomenclature is used to specify the compounds of formula I: the nitrogen atom $\underline{N}$—$R_2$ in the tetrahydropyran ring in formula I is designated "N". For example, N-BOC-staurosporin is a staurosporin derivative in which the radical $R_2$ is BOC. The nitrogen atom $\underline{N}$—$R_1$, on the other hand, is designated "6", as will be apparent from the numbering given in formula I. For example, 6-methyl-staurosporin is a staurosporin derivative in which the radical $R_1$ is methyl.

Abbreviations

BOC: tertiary butoxycarbonyl
DMF: dimethylformamide
HPLC: high-pressure liquid chromatography
THF: tetrahydrofuran

EXAMPLE 1

0.7 g (0.0012 mol) of N-BOC-6-methyl-staurosporin is dissolved in 4 ml of ethyl acetate and, at room temperature, 4 ml of an ethyl acetate solution saturated with hydrochloric acid are added thereto. After 3.5 hours, the suspension is partitioned between ethyl acetate and sodium hydrogen carbonate solution, and the organic phase is separated, dried over sodium sulfate and concentrated by evaporation. Flash-chromatography on silica gel 60 using ethyl acetate/ethanol (8:2) yields 6-methyl-staurosporin, m.p. 210°–215° C., $R_f$=0.28 (ethyl acetate:ethanol=8:2).

The starting material is obtained as follows:

Step 1.1

2.2 ml of a 1-molar solution of sodium bis(trimethylsilyl)amide in tetrahydrofuran are added at room temperature under a nitrogen atmosphere to a solution of 1.13 g (0.002 mol) of N-BOC-staurosporin (described in Example 36 of EP-A-296110) in 10 ml of dry dimethylformamide and stirring is carried out for 1 hour. A solution of 0.14 ml (0.0022 mol) of methyl iodide in 2 ml of dimethylformamide is then added dropwise and stirring is continued at room temperature for 2 hours. The reaction mixture is poured onto ice and extracted with ethyl acetate. The organic phase is washed with cold 0.1-normal hydrochloric acid, dried over sodium sulfate and concentrated by evaporation. The residue is separated by means of flash-chromatography on silica gel (type 60, Merck, Darmstadt, Germany). Ethyl acetate/petroleum ether (1:1) are used as eluant. Two compounds that are separate from each other are obtained from the individual fractions, namely N-BOC-6-methyl-7-oxo-staurosporin, m.p. 180°–185° C., $R_f$=0.58 (methylene chloride:ethanol=95:5), and N-BOC-6-methyl-staurosporin, m.p. 225°–228° C., $R_f$=0.45 (methylene chloride:ethanol=95:5).

EXAMPLE 2

Analogously to Example 1, there is obtained from 175 mg (0.0003 mol) of N-BOC-6-methyl-7-oxo-staurosporin (see Step 1.1), after a reaction time of 12 hours, 6-methyl-7-oxo-staurosporin; m.p. 180°–185° C., $R_f$=0.41 (ethyl acetate:ethanol=8:2).

EXAMPLE 3

4.4 g (7.7 mmol) of N-benzoyl-staurosporin are added to a suspension of 350 mg (11.5 mmol) of an 80% sodium hydride dispersion in white oil in 200 ml of absolute tetrahydrofuran. The mixture is stirred at room temperature for 4 hours. 1.4 ml (11.5 mmol) of benzyl bromide are then added and the reaction mixture is stirred at room temperature for a further 56 hours. For hydrolysis, 40 ml of water are added. The reaction mixture is then diluted with methylene chloride and the organic phase is separated, washed with 0.1-normal hydrochloric acid, dried over sodium sulfate, filtered and concentrated by evaporation. The residue is purified by means of flash-chromatography (ethyl acetate:petroleum ether=1:1). N-benzoyl-6-benzyl-staurosporin is obtained in the form of a yellow foam; $R_f$=0.48 (ethyl acetate:petroleum ether=1:1).

EXAMPLE 4

20 μl (0.18 mmol) of benzoyl chloride are added at room temperature to 75 mg (0.15 mmol) of 6-methyl-staurosporin (see Example 1) and 38 μl (0.225 mmol) of N,N-diisopropylethylamine in 5 ml of methylene chloride, and the reaction mixture is stirred at room temperature for one hour. It is then washed with saturated sodium hydrogen carbonate solution, dried over sodium sulfate and concentrated by evaporation. Flash-chromatography of the residue on silica gel 60 (methylene chloride:ethanol=98:2) yields N-benzoyl-6-methyl-staurosporin; m.p. 225°–227° C., $R_f$=0.47 (methylene chloride:ethanol=95:5).

EXAMPLE 5

Analogously to Example 1, there is obtained from 0.55 g (0.84 mmol) of N-BOC-6-benzyl-staurosporin, 6-benzyl-staurosporin; m.p. 187°–190° C., $R_f$=0.34 (methylene chloride:ethanol=95:5).

EXAMPLE 6

Analogously to Example 3, there is obtained from N-benzoyl-staurosporin and bromoacetic acid methyl ester N-benzoyl-6-methoxycarbonylmethyl-staurosporin; $R_f$=0.41 (chloroform:ethyl acetate=3:1).

EXAMPLE 7

Analogously to the processes described in this text, N-[(L)-alanyl]-6-benzylstaurosporin is obtained by reaction of 6-benzyl-staurosporin with N-benzyloxycarbonyl-L-alanine in absolute N,N-dimethylformamide in the presence of 1-hydroxybenzotriazole and 54.3 mg (0.283 mmol) of N-ethyl-N'-(3-diaminopropyl)-carbodiimide hydrochloride (EDC) and subsequent removal of the benzyloxycarbonyl protecting group by hydrogenation with $H_2$/Pd/C.

EXAMPLE 8

By reaction of 6-benzyl-staurosporin with N-BOC-L-alanine in absolute N,N-dimethylformamide in the presence of 1-hydroxybenzotriazole and N-ethyl-N'-(3-diaminopropyl)-carbodiimide hydrochloride (EDC) there is obtained N-[N-BOC-(L)-alanyl]-6-benzyl-staurosporin; m.p. 262°–264° C., $R_f$=0.79 (methylene chloride:methanol=95:5), $R_f$=0.50 (ethyl acetate:hexane=4:1).

EXAMPLE 9

From N-[N-BOC-(L)-alanyl]-6-benzyl-staurosporin (see Example 8) there is obtained by removal of the BOC protecting group by means of 4-normal hydrochloric acid in dioxane N-[(L)-alanyl]-6-benzyl-staurosporin hydrochloride; m.p. 299°–304° C. (with decomposition), $R_f$=0.69 (methylene chloride:methanol=4:1), $R_f$=0.42 (methylene chloride:methanol=9:1).

EXAMPLE 10

Human KB-31 (sensitive) and KB-8511 (drug-resistant, P-glycoprotein [Pgp] overexpressing) cells are incubated under a 5% carbon dioxide atmosphere in MEM-Alpha-Medium, with the addition of ribonucleosides and deoxyribonucleosides and in the presence of 5% foetal calf serum, 50 units/ml of the antibiotic penicillin and 50 μg/ml of the antibiotic streptomycin. The KB-8511 cells are kept as stock in the presence of 10 ng/ml of the antineoplastically active substance Colcemid (demecolcine). To determine the inhibition of the cell growth, batches of 1500 cells (without the addition of Colcemid) are sown in 96-well microtitre plates and incubated overnight under the conditions mentioned above. The test substance (A: the antineoplastically active substance vinblastine, B: the compound of formula I N-benzoyl-6-benzyl-staurosporin) is added in serial dilutions on day 1. The plates are then incubated under the conditions mentioned above for 4 days. During that time, the control cells undergo several cell divisions. After incubation, the cells are fixed with 3.3% (w/v) aqueous glutaraldehyde solution, washed with water and stained with 0.05% (w/v) methylene blue solution. After washing, the dye is eluted with 3% (w/v) aqueous hydrochloric acid. The optical density (OD) per well, which is directly proportional to the number of cells, is then measured with a photometer at 665 nm. The $IC_{50}$ values are calculated by means of a computer system, using the formula $$[OD_{665}(test)-OD_{665}(start)]/[OD_{665}(control)-OD_{665}(start)] \times 100$$

The $IC_{50}$ values are defined as being those concentrations of active ingredient at which the number of cells per well at the end of the incubation period amounts to only 50% of the number of cells in the control cultures.

| test substance [concentration] | % growth of KB 8511 cells: |
|---|---|
| A [2.34 ng/ml] | 101 |
| A [4.69 ng/ml] | 101 |
| A [9.38 ng/ml] | 98 |
| A [18.8 ng/ml] | 98 |
| A [37.5 ng/ml] | 98 |
| A [75.0 ng/ml] | 90 |
| A [150 ng/ml] | 66 |
| A [300 ng/ml] | 14 |
| B [1 μmol] | 95 |
| B [1 μmol] + A [2.34 ng/ml] | 0 |
| B [1 μmol] + A [4.69 ng/ml] | 0 |
| B [1 μmol] + A [9.38 ng/ml] | 0 |
| B [1 μmol] + A [18.8 ng/ml] | 0 |
| B [1 μmol] + A [37.5 ng/ml] | 0 |
| B [1 μmol] + A [75.0 ng/ml] | 0 |
| B [1 μmol] + A [150 ng/ml] | 0 |

-continued

| test substance [concentration] | % growth of KB 8511 cells: |
|---|---|
| B [1 μmol] + A [300 ng/ml] | 0 |
| B [0.1 μmol] | 92 |
| B [0.1 μmol] + A [2.34 ng/ml] | 91 |
| B [0.1 μmol] + A [4.69 ng/ml] | 81 |
| B [0.1 μmol] + A [9.38 ng/ml] | 74 |
| B [0.1 μmol] + A [18.8 ng/ml] | 66 |
| B [0.1 μmol] + A [37.5 ng/ml] | 52 |
| B [0.1 μmol] + A [75.0 ng/ml] | 28 |
| B [0.1 μmol] + A [150 ng/ml] | 6 |
| B [0.1 μmol] + A [300 ng/ml] | 0 | test substance A: vinblastine
test substance B: N-benzoyl-6-benzyl-staurosporin

EXAMPLE 11

The following results are obtained analogously to Example 10, using the antineoplastically active test substance adriamycin (C) instead of vinblastine (A):

| test substance [concentration] | % growth of KB 8511 cells: |
|---|---|
| C [1.56 ng/ml] | 99 |
| C [3.13 ng/ml] | 100 |
| C [6.25 ng/ml] | 97 |
| C [12.5 ng/ml] | 101 |
| C [25 ng/ml] | 99 |
| C [50 ng/ml] | 97 |
| C [100 ng/ml] | 96 |
| C [200 ng/ml] | 93 |
| B [1 μmol] | 82 |
| B [1 μmol] + A [1.56 ng/ml] | 90 |
| B [1 μmol] + A [3.13 ng/ml] | 89 |
| B [1 μmol] + A [6.25 ng/ml] | 82 |
| B [1 μmol] + A [12.5 ng/ml] | 56 |
| B [1 μmol] + A [25 ng/ml] | 14 |
| B [1 μmol] + A [50 ng/ml] | 1 |
| B [1 μmol] + A [100 ng/ml] | 4 |
| B [1 μmol] + A [200 ng/ml] | 7 | test substance C: adriamycin
test substance B: N-benzoyl-6-benzyl-staurosporin

EXAMPLE 12

The determination of the in vivo antitumour activity of test substance B (=N-benzoyl-6-benzyl-staurosporin) against the drug-sensitive parental KB-31 and a multidrug-resistant variant of the KB-31, i.e. the multidrug-resistant variant KB-8511, tumours is carried out in female Balb/c nude mice (Bomholdgaard, Copenhagen, Denmark) bearing serially passaged (minimum of three consecutive transplantations) either the human parental drug-sensitive KB-31 tumours or the human KB-8511 tumours. The KB-8511 tumours overexpress Pgb, the product of the mdr-1 gene (S. Akiyma et al., "Isolation and genetic characterization of human KB cell lines resistant to multiple drug", Somatic Cell and Mol. Gen. 11, 117–126 [1985]). Tumour fragments of approximately 25 mg are transplanted into the left flank of each animal (n=6 per group). Treatment is started when the tumours reach a mean tumour volume of 150–200 mm$^3$:25 mg/kg p.o. of the test substance B are given once as a single dose 4 hours prior to a single application of 9.0 mg/kg i.v. of adriamycin at day 7 after tumour transplantation. Tumour growth is monitored twice weekly by measuring perpendicular diameters. Tumour volumes are determined as described by T. Meyer et al., Int. J. Cancer 43, 851–856 (1989), and expressed as relative tumour size (i.e. the increase in tumour volume compared with the tumour volume at the start of the treatment). Maximal tumour regression, expressed in %, i.e. the decrease in tumour volume compared with the volume at the start of the treatment, was reached by the mixture of substance B (1×25 mg/kg p.o.) and adriamycin (1×9 mg/kg i.v.) in the case of the KB-8511 tumour and amounted to 29% on day 6. In the case of the KB-31 tumour maximal tumour regression was reached by adriamycin (1×9 mg/kg i.v.) alone and amounted to 24% on day 5.

As is evident from the quotient [%] of the median tumour volumes in the treated versus the control groups, i.e. the T/C-values [%] in the following table, test substance B sensitises the multi-drug resistant KB-8511 tumours to adriamycin and restores the activity of adriamycin against the KB-8511 tumours to an extent similar to the activity of adriamycin against the adriamycin sensitive KB-31 tumours. The smaller the T/C values [%], the more active the given dose.

| tumour | compound | dose | T/C [%] |
|---|---|---|---|
| KB-31 | placebo | 1 × 10 ml/kg i.v. | 100 |
| KB-31 | substance B | 1 × 25 mg/kg p.o. | 91 |
| KB-31 | adriamycin | 1 × 9 mg/kg i.v. | 13 |
| KB-8511 | placebo | 2 × 10 ml/kg i.v. | 100 |
| KB-8511 | substance B | 1 × 25 mg/kg p.o. | 93 |
| KB-8511 | adriamycin | 1 × 9 mg/kg i.v. | 89 |
| KB-8511 | substance B and adriamycin | 1 × 25 mg/kg p.o. 1 × 9 mg/kg i.v. | 11 |

EXAMPLE 13

Tablets, each comprising 20 mg of active ingredient, for example one of the compounds of formula I described in the preceding Examples, are prepared in the usual manner with the following composition:
Composition

| active ingredient | 20 mg |
|---|---|
| wheat starch | 60 mg |
| lactose | 50 mg |
| colloidal silicic acid | 5 mg |
| talc | 9 mg |
| magnesium stearate | 1 mg |
| | 145 mg |

Preparation

The active ingredient is mixed with a portion of the wheat starch, with the lactose and the colloidal silicic acid, and the mixture is forced through a sieve. A further portion of the wheat starch is made into a paste with 5 times the amount of water on a water bath and the powder mixture is kneaded with that paste until a slightly plastic mass has been produced.

The plastic mass is pressed through a sieve of approximately 3 mm mesh size and dried, and the resulting dry granules are forced through a sieve once more. The remainder of the wheat starch, the talc and the magnesium stearate are then added and the mixture is compressed to form tablets each weighing 145 mg and having a breaking notch.

EXAMPLE 14

Capsules, each comprising 25 mg of active ingredient, for example one of the compounds of formula I described in the preceding Examples, are prepared as follows:

Composition

| active ingredient | 25.0 mg |
|---|---|
| gelucire 44/14 | 183.3 mg |

(gelucire 44/14 is a mixture of esters of saturated $C_8$–$C_{18}$-fatty acids with glycerol and polyethylene glycol having a molecular weight of approximately 1500; produced by: Gatte-fossé, F-69800 Saint Priest, France).

Preparation

A portion of the gelucire 44/14 is melted at a temperature of from 50° C. to 100° C. The active ingredient is mixed with the liquid gelucire 44/14 in a heated mortar to form a paste. The remainder of the gelucire 44/14 is then also melted and is added to the paste. The mixture is stirred at 50° C. until a solution is obtained. This is introduced into the capsules while warm and is cooled. The wax so obtained comprises 12% by weight active ingredient.

The wax-like dispersion can also be processed in water by ultrasound treatment to form a milky liquid that can be administered orally.

What is claimed is:

1. A method of removing existing multi-drug resistance or of avoiding the development of multi-drug resistance in a warm-blooded animal in need of such treatment, which method comprises the administration to that warm-blooded animal of a staurosporin derivative of formula I

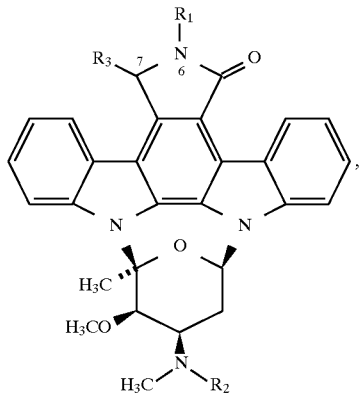

wherein $R_1$ is formyl, an aliphatic hydrocarbon radical having up to 29 carbon atoms that is unsubstituted or substituted by aryl, or is an aryl radical, $R_2$ is hydrogen, $C_1$–$C_5$alkyl, benzoyl, lower alkanoyl or α-aminoacyl having a free or protected amino group, and $R_3$ is hydrogen, hydroxy, lower alkoxy or oxo, or wherein $R_1$ is methoxycarbonylmethyl, $R_2$ is benzoyl, and $R_3$ is hydrogen, or of a pharmaceutically acceptable salt of such a compound of formula I having at least one salt-forming group, in an effective dose that removes multi-drug resistance or avoids the development thereof.

2. The method according to claim 1, wherein $R_1$ is an unsubstituted aliphatic hydrocarbon radical having up to 29 carbon atoms that is other than lower alkyl, or is an aliphatic hydrocarbon radical having up to 29 carbon atoms that is substituted by aryl, or is an aryl radical.

3. The method according to claim 1, wherein $R_1$ is lower alkyl or benzyl, $R_2$ is hydrogen, benzoyl or α-aminoacyl selected from glycyl, phenylglycyl, alanyl, phenylalanyl, prolyl, leucyl, seryl, valyl, tyrosyl, arginyl, histidyl and asparagyl, and $R_3$ is hydrogen or oxo, or wherein $R_1$ is methoxycarbonylmethyl, $R_2$ is benzoyl and $R_3$ is hydrogen.

* * * * *